US00PP27096P2

(12) United States Plant Patent
Hartman

(10) Patent No.: US PP27,096 P2
(45) Date of Patent: Aug. 23, 2016

(54) ***CALADIUM* PLANT NAMED 'RED ALERT'**

(50) Latin Name: *Caladium×hortulanum*
Varietal Denomination: Red Alert

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 90 days.

(21) Appl. No.: 14/544,170

(22) Filed: Dec. 4, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Red Alert', characterized by its compact, upright and uniformly mounded plant habit; vigorous growth habit and rapid growth rate; fancy-type leaves with red-colored centers with rose red-colored venation and surrounded by dark green-colored borders; and good landscape performance and sun tolerance.

4 Drawing Sheets

Botanical designation: *Caladium×hortulanum.*
Cultivar denomination: 'RED ALERT'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Red Alert'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor on Apr. 15, 2007 in Avon Park, Fla. of *Caladium×hortulanum* 'Pink Beauty', not patented, as the female, or seed, parent with *Caladium×hortulanum* 'Florida Red Ruffles', disclosed in U.S. Plant Pat. No. 13,136, as the male, or pollen, parent. The new *Caladium* plant was discovered and selected by the Inventor as a single plant within the progeny of the stated cross-pollination in a controlled outdoor nursery environment in Zolfo Springs, Fla. on Sep. 15, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since Apr. 15, 2009 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Red Alert'.

These characteristics in combination distinguish 'Red Alert' as a new and distinct *Caladium* plant:

1. Compact, upright and uniformly mounded plant habit.
2. Vigorous growth habit and rapid growth rate.
3. Fancy-type leaves with red-colored centers with rose red-colored venation and surrounded by dark green-colored borders.
4. Good landscape performance and sun tolerant.

Plants of the new *Caladium* differ primarily from plants of the female parent, 'Pink Beauty', in the following characteristics:

1. Plants of the new *Caladium* are more compact and mounding than plants of 'Pink Beauty'.
2. Plants of the new *Caladium* and 'Pink Beauty' differ in leaf color as leaves of plants of 'Pink Beauty' are olive green in color with pink-colored blotches.
3. Plants of the new *Caladium* and 'Pink Beauty' differ in leaf petiole color as leaf petioles of plants of 'Pink Beauty' are green to tank pink in color with darker green-colored tessellations, streaks and speckles.

Plants of the new *Caladium* differ primarily from plants of the male parent, 'Florida Red Ruffles', in the following characteristics:

1. Plants of the new *Caladium* are faster growing and produce finished plants about one week earlier than plants of 'Florida Red Ruffles'.
2. Plants of the new *Caladium* and 'Florida Red Ruffles' differ in leaf shape and color as leaves of plants of 'Florida Red Ruffles' are lance-types with dark red-colored centers and venation with green-colored margins.
3. Plants of the new *Caladium* and 'Florida Red Ruffles' differ in leaf petiole color as leaf petioles of plants of 'Florida Red Ruffles' are almost black in color with tanned pink-colored stripes.

Plants of the new *Caladium* can be compared to plants of *Caladium×hortulanum* 'Freida Hemple', not patented. In side-by-side comparisons, plants of the new *Caladium* differed primarily from plants of 'Freida Hemple' in the following characteristics:

1. Plants of the new *Caladium* were more compact than plants of 'Freida Hemple'.
2. Plants of the new *Caladium* and 'Freida Hemple' differed in leaf color as leaves of plants of 'Freida Hemple' had bright red-colored centers and medium green-colored margins.
3. Plants of the new *Caladium* and 'Freida Hemple' differed in leaf petiole color as leaf petioles of plants of 'Freida Hemple' were tan pink in color with dense black brown-colored streaks and stippling.

Plants of the new *Caladium* can also be compared to plants of *Caladium×hortulanum* 'John Peed', not patented. In side-by-side comparisons, plants of the new *Caladium* differed primarily from plants of 'John Peed' in the following characteristics:

1. Plants of the new *Caladium* were more compact and mounding than plants of 'John Peed'.
2. Plants of the new *Caladium* were faster growing and produce finished plants about two weeks earlier than plants of 'John Peed'.
3. Plants of the new *Caladium* and 'John Peed' differed in leaf color as leaves of plants of 'John Peed' had dark red-colored centers and dark green-colored margins.
4. Plants of the new *Caladium* and 'John Peed' differed in leaf petiole color as leaf petioles of plants of 'John Peed' were dark pink in color with dark green to almost black-colored stippling and streaks.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Red Alert' in a container and grown in a shadehouse (tuber not de-eyed).

The photograph at the top of the second sheet is a comparison view of typical potted plants of the female parent, 'Pink Beauty' (left), 'Red Alert' (center) and the male parent, 'Florida Red Ruffles' (right).

The photograph at the bottom of the second sheet is a comparison view of typical potted plants of 'John Peed' (left), 'Red Alert' (center) and 'Frieda Hemple' (right).

The photograph at the top of the third sheet is a comparison view of typical plants of 'Red Alert' grown in containers; the plant on the left has not had its tuber de-eyed and the plant on the right has had its tuber de-eyed prior to planting.

The photograph at the bottom of the third sheet is a close-up view of typical freshly-harvested tubers and roots of 'Red Alert'.

The photograph at the top of the fourth sheet is a side perspective view of typical plants of 'Red Alert' grown in an open field.

The photograph at the bottom of the fourth sheet is a close-up view of a typical inflorescence of 'Red Alert'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were 7.5 weeks old, and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Red Alert'.

Parentage:

*Female, or seed, parent.*—*Caladium×hortulanum* 'Pink Beauty', not patented.

*Male, or pollen, parent.*—*Caladium×hortulanum* 'Florida Red Ruffles', disclosed in U.S. Plant Pat. No. 13,136.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments ovate, elliptic or irregular in shape. Height: About 2.9 cm. Diameter: About 4.4 cm to 6 cm. Segment height: About 2.1 cm to 2.5 cm. Segment diameter: About 2.4 cm to 2.6 cm. Texture: Thick, starchy; somewhat brittle. Color: Epidermis, freshly-harvested: Close to 199A to 199B. Epidermis, dried: Close to 200A. Cortical tissue: Close to 4D. Axillary buds: Close to 155C and 29D. Root description: Thick, fleshy contractile roots; color, close to 155C. Rooting habit: Medium density.

Plant description:

*Plant type.*—Herbaceous perennial; suitable as a potted plant in containers 15-cm to 25-cm and suitable as a landscape plant in shaded and sunny areas.

*Plant and growth habit.*—Compact, upright and uniformly mounded plant habit; vigorous and dense growth habit; rapid growth rate, potted plants in finished or saleable form in about seven weeks after planting tubers; leaf petioles and leaves arise from one or more growing points on tubers; petioles mostly upright and leaning outwardly with development.

*Plant height, from soil level to top of foliar plane, shadehouse-grown potted plants.*—About 27 cm to 31 cm.

*Plant height, from soil level to top of inflorescences, shadehouse-grown potted plants.*—About 23.5 cm.

*Plant diameter or spread, shadehouse-grown potted plants.*—About 37 cm to 41 cm.

*Number of shoots per plant, shadehouse-grown potted plants, tubers not de-eyed.*—About three develop per #1 tuber.

*Number of shoots per plant, shadehouse-grown potted plants, tubers de-eyed.*—About three to four develop per #1 tuber.

*Cataphylls, shadehouse-grown potted plants.*—Length: About 4.2 cm to 5 cm. Width: About 1.1 cm to 1.5 cm. Shape: Wedge-shaped. Apex: Acute to cuspidate. Base: Sheathing the stem. Color, inner surface: Close to N155C and N170D; colors and patterns of the outside surface are visible on the inner surface. Color, outer surface: Close to N170D tinged with close to 147C faintly and variably tinged with close to 185D; with development, color becoming closer to 200A to 200B and 199A stained with close to 187A.

Leaf description:

*Arrangement and type.*—Alternate; simple; fancy-type.

*Length, shadehouse-grown potted plants.*—About 11.5 cm to 17 cm.

*Width, shadehouse-grown potted plants, flattened.*—About 9.8 cm to 13.5 cm.

*Shape.*—Broadly ovate.

*Apex.*—Acute to acuminate.

*Base.*—Sagittate to peltate.

*Margin.*—Entire; mostly flat with broad undulations.

*Texture, upper and lower surfaces.*—Smooth, glabrous.

*Luster, upper surface.*—Dull sheen.

*Luster, lower surface.*—Glaucous, dull sheen.

*Venation pattern.*—Pinnate.

*Color, shadehouse-grown potted plants.*—Developing leaves, upper surface: Main colors: Interveinal areas, close to N186C; towards the margins, close to 147A tinged with close to N189A. Margins: Close to 147A tinged with close to N189A. Basal notch: Close to 187A. Midrib and primary venation: Close to 53A tinged with close to 185B; areas adjacent to venation, close to 185B. Developing leaves, lower surface: Main color: Close to between 191A and 189A. Margins: Close to between 191A and 189A. Basal notch: Close to 187A to 187B. Midrib and primary venation: Close to 185B to 185C; areas adjacent to venation, close to 184B. Secondary venation: Close to N189A to N189B. Fully expanded leaves, upper surface: Main colors: Interveinal areas, close to N186C; towards the margins, close to 147A and N189A. Margins: Close to 147A and N189A. Basal notch: Close to 187A. Midrib and primary venation: Close to 53A tinged with close to 185B; areas adjacent to venation, close to 185B. Fully expanded leaves, lower surface: Main color: Close to between 191A and 189A. Margins: Close to between 191A and 189A. Basal notch: Close to 187A. Midrib and primary venation: Close to 185B; areas adjacent to venation, close to 184B. Secondary venation: Close to N189A.

*Petioles.*—Aspect: Initially upright and straight; with development, leaning outwardly; flexible. Length, shadehouse-grown potted plants: About 19 cm to 27 cm. Diameter, distal, shadehouse-grown potted plants: About 3 mm to 3.5 mm. Diameter, proximal, shadehouse-grown potted plants: About 6 mm to 8 mm. Texture: Smooth, glabrous; glaucous. Color, shadehouse-grown potted plants, Just below the leaf and petiole junction: Close to 185D. Overall: Close to N170D tinged with close to 185D and 147B to 147C, stippled and streaked with close to 147A tinged with close to N199A. Wing length, shadehouse-grown potted plants: About 4.5 cm to 6.6 cm. Wing diameter, shadehouse-grown potted plants: About 6 mm. Texture, inner and outer surfaces: Smooth, glabrous. Wing color, shadehouse-grown potted plants, inner surface: Close to 155C and N170D. Wing color, shadehouse-grown potted plants, outer surface: Close to N170D tinged with close to 147C or faintly and variably tinged with close to 185D.

Inflorescence description: Inflorescences observed on seven week-old shadehouse-grown potted plants.

*Inflorescence arrangement.*—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; sweet, jasmine-like with camphor note.

*Natural flowering season and flower longevity.*—Plants of the new *Caladium* typically flower during the spring in central Florida; early flowering habit, flowers develop about seven weeks after growth commences; inflorescences last about three days before fading; inflorescences persistent.

*Spathe.*—Length, overall: About 7 cm. Length, distal open portion: About 4.5 cm. Length, proximal closed portion: About 2.5 cm. Width, distal open portion: About 2.4 cm. Width, at constriction: About 1 cm. Width, proximal closed portion: About 1.9 cm. Shape: Elliptic. Apex: Acute. Base: Obtuse. Margin: Entire. Texture, front and rear surfaces: Smooth, glabrous. Luster, front surface: Dull sheen. Luster, rear surface: Glaucous. Color, front surface: Distal open portion: Close to 155A; with development, color becoming closer to 199C to 199D. Proximal closed portion: Close to 194B; towards the base, close to N186D and 187C; color does not change with development. Color, rear surface: Distal open portion: Close to 155A and 155C; color does not change with development. Proximal closed portion: Close to 182B and 183C occasionally streaked and flecked with close to 148D; color does not change with development.

*Spadix.*—Length: About 5.1 cm. Length, male flower zone: About 3.1 cm. Length, sterile zone: About 1.1 cm. Length, female flower zone: About 9 mm. Diameter, male flower zone: About 7.5 mm. Diameter, sterile flower zone: About 5 mm. Diameter, female flower zone: About 8 mm. Shape: Columnar. Apex: Obtuse to bluntly acute. Base: Obtuse. Aspect: Upright. Color, mature, male zone: Close to 11D. Color, mature, sterile zone: Close to 11D. Color, mature, female zone: Close to 10D and 155A. Male flowers: Quantity per spadix: About 90. Shape: Obovate. Height: About 3 mm. Diameter: About 2 mm. Pollen amount: Sparse. Pollen color: Close to 4C. Female flowers: Quantity per spadix: About 98. Shape: Obovate. Height: About 3 mm. Diameter: About 1 mm. Stigma color: Close to 10D. Ovary color: Close to 155A.

*Scape.*—Length: About 16.5 cm. Diameter: About 4 mm. Strength: Sturdy; flexible. Aspect: Mostly erect. Texture: Smooth, glabrous; glaucous. Color, just below spathe: Close to 195A and 199B, streaked and stippled with close to 183C. Color, overall: Close to 195A streaked and stippled with close to 199A tinged with close to 183D.

*Seeds and fruits*.—To date, seed and fruit development have not been observed on plants of the new *Caladium*.

Disease & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Red Alert' as illustrated and described.

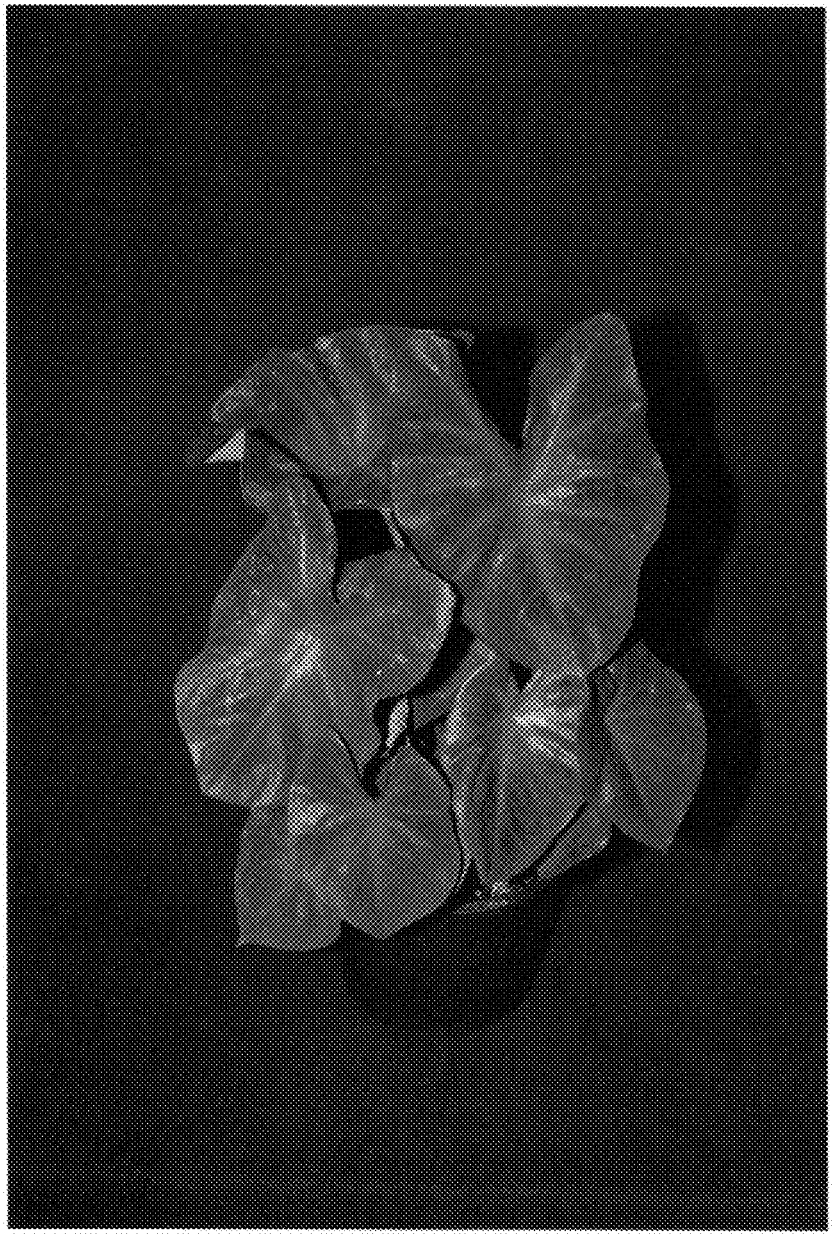

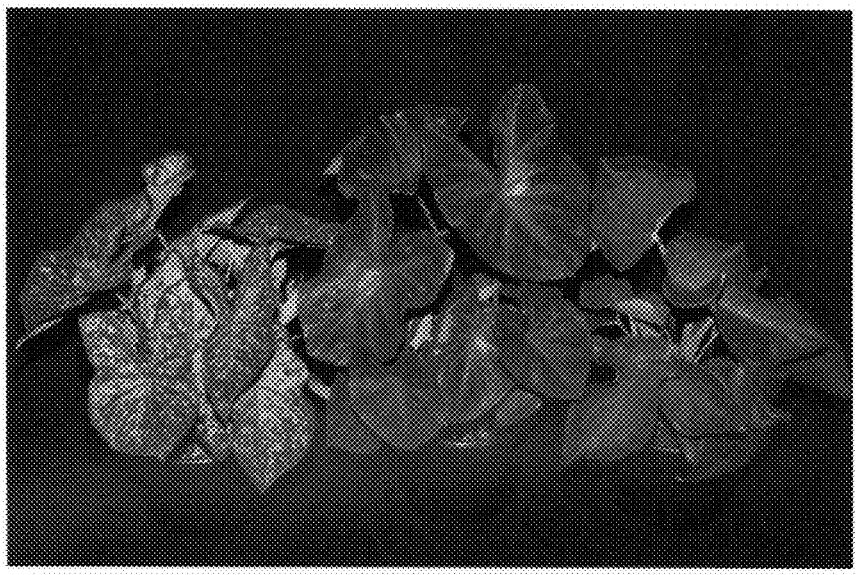
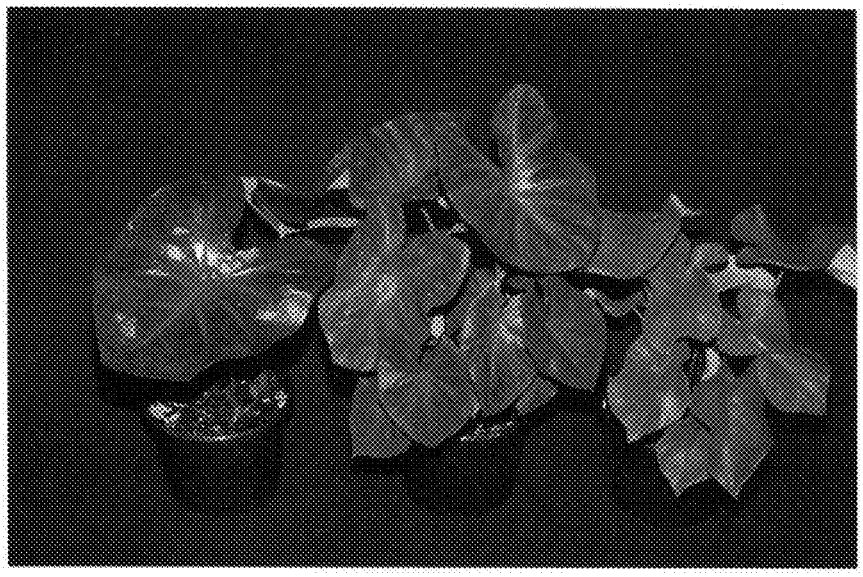

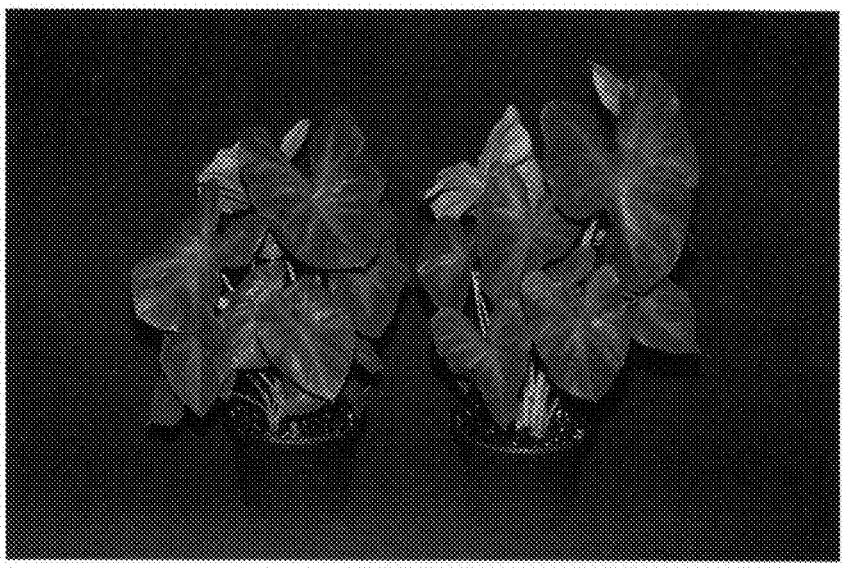
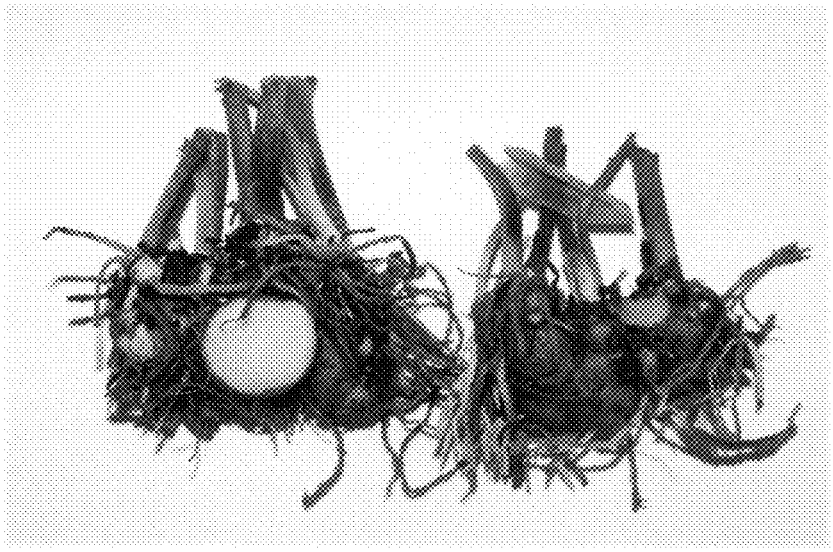

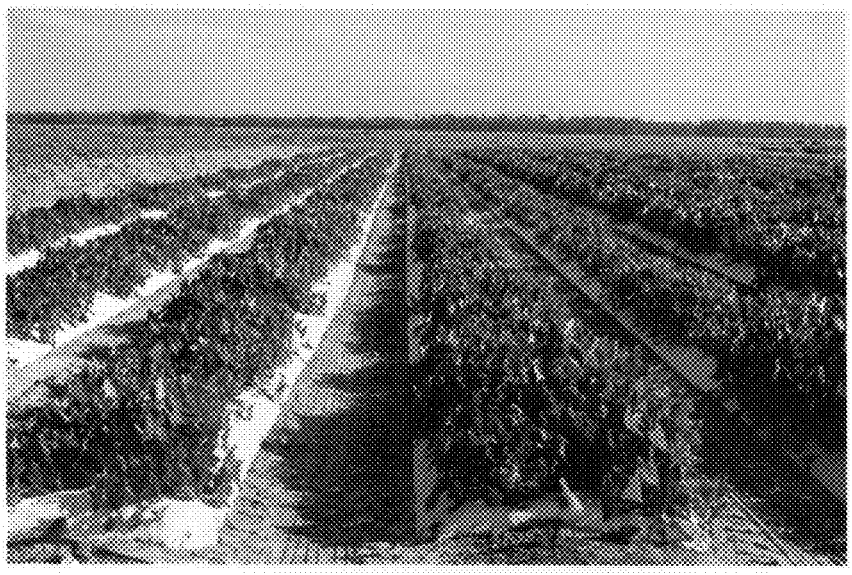
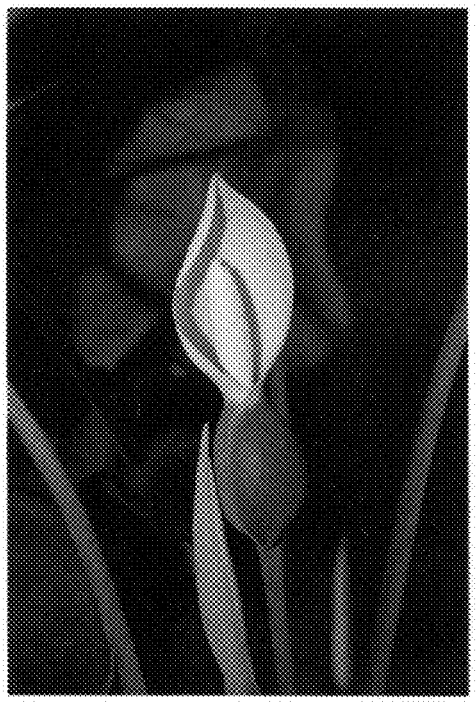

* * * * *